(12) United States Patent
Heuft

(10) Patent No.: US 6,239,870 B1
(45) Date of Patent: May 29, 2001

(54) METHOD FOR IDENTIFYING MATERIALS, IMPURITIES AND RELATED DEFECTS WITH DIFFUSE DISPERSION TRANSPARENT OBJECTS

(75) Inventor: Bernhard Heuft, Burgbrohl (DE)

(73) Assignee: Heuft Systemtechnik GmbH, Burgbrohl (DE)

( * ) Notice: Subject to any disclaimer, the term of this patent is extended or adjusted under 35 U.S.C. 154(b) by 0 days.

(21) Appl. No.: 09/508,137
(22) PCT Filed: Sep. 21, 1998
(86) PCT No.: PCT/EP98/06014
§ 371 Date: Mar. 7, 2000
§ 102(e) Date: Mar. 7, 2000
(87) PCT Pub. No.: WO99/15882
PCT Pub. Date: Apr. 1, 1999

(30) Foreign Application Priority Data

Sep. 19, 1997 (DE) .............................. 197 41 384

(51) Int. Cl.[7] .................................................. G01N 21/00
(52) U.S. Cl. ................... 356/239.5; 250/223 B; 348/127
(58) Field of Search .............................. 356/239.1, 239.4, 356/239.5, 239.7, 239.8, 240.1; 250/223 B; 348/127, 125; 382/142

(56) References Cited

U.S. PATENT DOCUMENTS

| | | | |
|---|---|---|---|
| 4,310,242 | 1/1982 | Genco et al. | 356/128 |
| 4,547,067 | * 10/1985 | Watanabe | 356/239.4 |
| 4,983,822 | * 1/1991 | Fukuchi | 250/223 B |
| 5,243,400 | * 9/1993 | Ringlien | 356/239.4 |
| 5,363,188 | 11/1994 | Didelot et al. | 356/124.5 |
| 5,621,520 | 4/1997 | Hoffman | 356/124.5 |
| 6,049,379 | * 4/2000 | Lucas | 356/240.1 |

FOREIGN PATENT DOCUMENTS

| | | | |
|---|---|---|---|
| 3443816A1 | 6/1985 | (DE) | G01M/11/02 |
| 19519777A1 | 12/1996 | (DE) | F21S/3/00 |
| 69304741T2 | 4/1997 | (DE) | G01N/21/89 |
| 0387930A1 | 9/1990 | (EP) | G01N/21/88 |
| 0491555A1 | 6/1992 | (EP) | G01N/21/90 |
| 0676635A1 | 10/1995 | (EP) | G01N/21/90 |

OTHER PUBLICATIONS

German Search Report, dated Mar. 18, 1998.

* cited by examiner

*Primary Examiner*—Hoa Q. Pham
(74) *Attorney, Agent, or Firm*—Gardner, Carton & Douglas

(57) ABSTRACT

Diffusely scattering defects are to be detected in items made from transparent material, e.g. drinks bottles. To this end, the items (10) are inspected using a light source (12) and a camera (16), a contrast pattern (14) being arranged between the light source (12) and the item to be inspected. Diffusely scattering defects are detected by a decrease in the contrast of the contrast pattern (14) reproduced through the item.

8 Claims, 2 Drawing Sheets

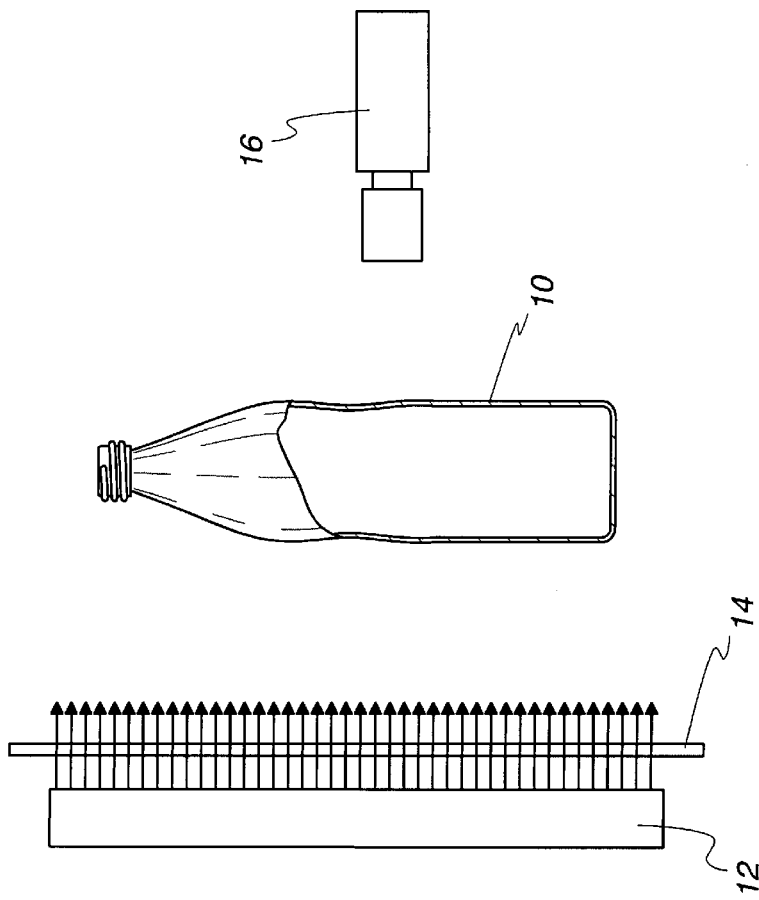
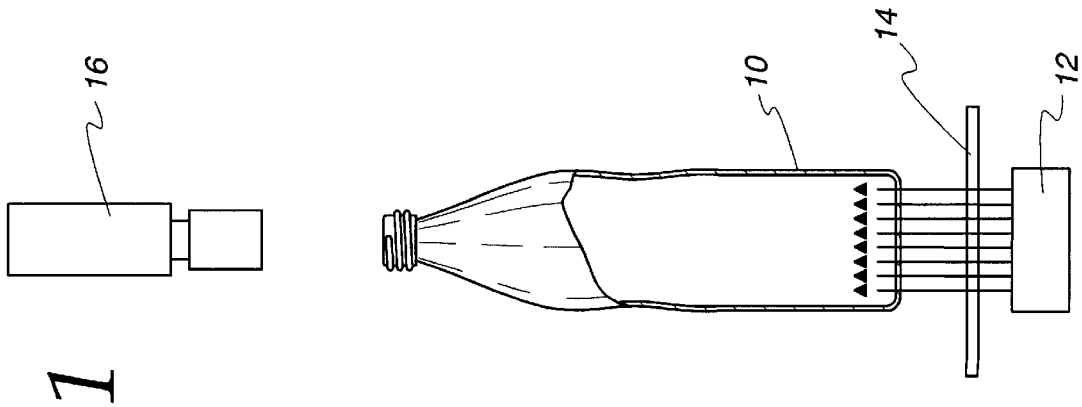

METHOD FOR IDENTIFYING MATERIALS, IMPURITIES AND RELATED DEFECTS WITH DIFFUSE DISPERSION TRANSPARENT OBJECTS

BACKGROUND OF THE INVENTION

The invention relates to a method for detecting diffusely scattering materials, impurities, deposits, damage or coatings of the surface or fluctuations in the material thickness in items made of transparent material, the items being transilluminated and examined by a light source and a camera.

Structureless, semi-transparent impurities of items made of transparent material such as glass, PET, PC, PVC and similar can often not be detected using conventional image-processing methods. Among such impurities are for example milky adhesive tapes, thin lacquer coats, rust and thin partly mineral deposits on the inside or outside of the wall of the items. Furthermore, the detection of changes on the surface of the transparent material, such as scratches covering large areas, abrasion traces, surface parts which are etched or sand-blasted as well as in general coatings which impair transparency is also problematic. Such semi-transparent defects slightly attenuate the light entering the camera from the light source in a straight line and diffuse it only slightly. Observed over a larger area, such a defect scarcely reduces brightness, particularly as a dispersion of the light which is brought about by the transparent material itself must also be taken into account. In processes which work with bright-field illumination, the detection of such defects or irregularities is therefore scarcely possible, as the image recorded by the camera shows neither contrasts, contrasts which could be additionally intensified by image processing methods, nor a great reduction in the brightness of the image.

Dark-field methods which are based on a change in the polarization of the light by defect to be detected (EP-A-0 387 930) are often not usable due to the polarization effects which occur in transparent container materials themselves. Other dark-field methods in which the optical axis of the camera stands at a right angle to the direction of illumination (EP-A-0 429 086) can often be carried out only with difficulty due to geometric boundary conditions, and the scatter caused by the semi-transparent defects is often not large enough for these processes.

SUMMARY OF THE INVENTION

The object of the invention is to enable structureless, semi-transparent impurities and defects as listed at the beginning to be detected.

This object is achieved according to the invention in that a contrast pattern is arranged between the light source and the item to be inspected and the contrast of the contrast pattern reproduced through the item is determined.

Semi-transparent materials with weak diffuse dispersion greatly change the optical transmission function. The reproduction of a sharp contour is blurred by this and the contrast weakened. With the method according to the invention, this is exploited to inspect transparent containers for semi-transparent diffusely scattering defects. The contrast pattern consists of transparent and non-transparent regions which are sharply delimited vis-à-vis each other so that when the contrast pattern is illuminated from the rear, maximum differences in brightness and thus a maximum contrast results. With the method according to the invention, such a contrast pattern is arranged between the light source and the transparent item to be inspected so that the item to be inspected is located in the beam path between the contrast pattern and the camera, and the contrast pattern is observed through the transparent item, the detection process otherwise proceeding as in a normal bright-field detection process. The contrast structure of the image recorded by the camera is analyzed using standard methods of image processing. Without semi-transparent defects, the transmission function is hardly disturbed, and in particular the intensity of the contrasts is retained. If on the other hand, a semi-transparent defect is present, the contrast intensity is reduced in the region of this defect, i.e. the brightness distribution becomes more even, as the brightness in the transparent regions of the pattern decreases whilst the brightness in the non-transparent regions of the pattern is increased. The resulting deviation from the target contrast can be detected as a defect.

The minimum size of the detectable defect corresponds approximately to the width of the light and dark regions of the contrast pattern. This width is in turn matched to the resolution of the optical system and possible distortions through the refraction of the light in the transparent material of the items.

Preferably, the camera is focussed on the plane in which the contrast pattern is arranged. The maximum contrast intensity is achieved by this focussing.

The greater the space between the contrast pattern and the item to be inspected, the more intense the effect of diffusely scattering defects on the contrast. However, the optical distortions of the contrast pattern caused by fractures in the material of the wall of the items also become greater as a result of an increase in this interval. A suitable compromise must be found here in each individual case.

Fluctuations in the material thickness of the wall of the items influence the reproduction of the contrast pattern shown in the focal plane of the camera. Such fluctuations act as an additional lens introduced into the beam path, whereby on the one hand the contrast pattern is shown distorted, and on the other hand the focussing for the corresponding image spot is lost. Overall, the contrast structure of the reproduction is thereby influenced such that fluctuations in the material thickness can be ascertained in similar fashion to semi-transparent defects by a decrease in the contrast. In this way, embossed structures in the wall of the items can also be located.

Using the method according to the invention, non-transparent defects can also be detected as these also lead to a change in the contrast. In this respect, however, there are no advantages compared with known bright-field detection methods.

The method according to the invention can be integrated into already existing inspection apparatuses, as the light source and the camera are already present. It can also be combined with other inspection processes. In order that the contrast pattern takes effect only with the inspection process according to the invention, it should be visible only under the optical conditions specified there. It must remain invisible for all other inspection processes. This is enabled by a spectral separation of the two inspection processes. To this end, the contrast pattern can be manufactured from a material in which the non-transparent regions block the beams only for the method according to the invention. The non-transparent regions can e.g. be non-transparent only for a particular wavelength, the contrast structure then being determined for this wavelength only. For the other inspection processes which require a roughly uniformly illuminated background surface, a different spectral range is then used in which the transmission of the contrast pattern is roughly uniform.

Alternatively, the inspection processes can also be separated by different polarization of the individual regions of the contrast pattern. For the method according to the invention, an analyzer is then used, the direction of polarization of which lies perpendicular to that of the dark regions. The other inspection processes are then carried out without such an analyzer so that the whole surface of the contrast pattern shows a uniform brightness.

Embodiments of the invention are shown in the following using the diagram. There are shown in:

BRIEF DESCRIPTION OF THE DRAWINGS

FIG. 1 an arrangement for the detection of semi-transparent defects on the bottom of a transparent drinks bottle;

FIG. 2 an arrangement for the detection of semi-transparent defects on the side wall of a transparent drinks bottle.

DETAILED DESCRIPTION OF THE DRAWINGS

Figure 3A:
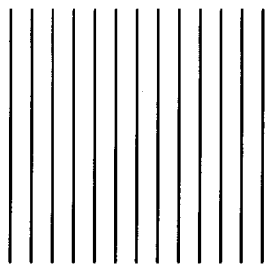
FIGS. 3a–3f examples of contrast patterns.

In the embodiment in FIG. 1, drinks bottles 10 are subjected to a bottom inspection, to which end the drinks bottles 10 e.g. are held and transported between laterally gripping pairs of belts. These transport apparatuses are generally known (EP-A-0 124 164) and are therefore not shown. The drinks bottles 10 are illuminated from below through a contrast pattern 14 using a flat light source 12, and a reproduction of the bottom of the drinks bottle 10 is produced through the opening of the drinks bottle 10 using a CCD camera 16.

The contrast pattern 14 is an arrangement of opaque strips 20, radiating out from a central point, between which transparent fields 21 are located. To this end, the contrast pattern 14 consists of a glass sheet onto which black stripes 20 are glued. The contrast pattern 14 is arranged centrally under the bottom of the drinks bottle 10.

The image evaluation procedure is as follows: the reproduction of the bottle bottom is scanned pointwise, in directions at right angles to each other, by means of the CCD camera 16. The brightness of each image spot is determined, and bright-dark and dark-bright transitions are ascertained by comparison with the brightness of adjacent image spots. Such a transition occurs e.g. whenever the scan crosses the border between a transparent region 21 and an opaque region 20 of the contrast pattern 14. The number of these transitions and the brightness contrast of the transitions is recorded, to which end the brightness contrast is divided for example into 250 shades of grey. Semi-transparent, diffusely scattering impurities lead to a shift to transitions with a smaller brightness difference. Semi-transparent, diffusely scattering impurities can therefore be detected by the fact that the number of transitions with a large brightness difference, i.e. a large number of shades of grey, fails to reach a threshold value. This threshold value is determined empirically in advance.

Figure 3B:
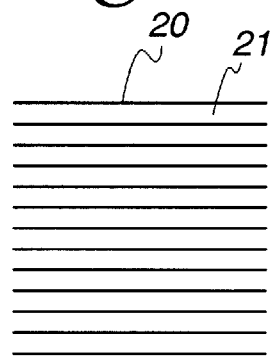
Figure 3C:
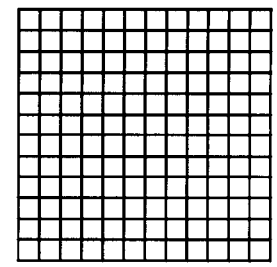
Figure 3D:
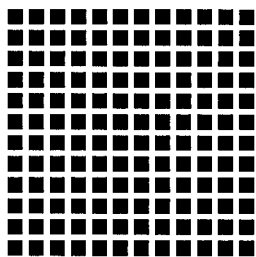
Figure 3E:
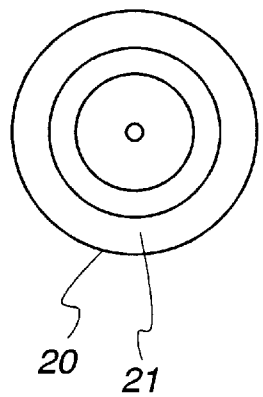
Figure 3F:
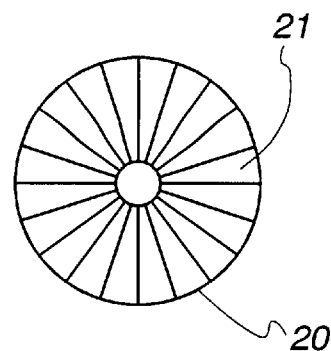

In the embodiment in FIG. 2, the drinks bottle 10 is inspected from the side. The light source 12 covers a correspondingly large surface and the contrast pattern 14 consists of horizontal parallel strips 20, 21 according to FIG. 3b. The contrast pattern 14 is in turn arranged between the light source 12 and the drinks bottle 10. The image evaluation procedure is analogous to that of FIG. 1.

In FIG. 3, examples of contrast patterns 14 are shown. In general, it is expedient to select a contrast pattern 14 which is changed as little as possible by the item to be inspected itself. The bottom of a drinks bottle generally shows fluctuations in thickness which are concentric to the center. Such fluctuations in thickness act as lenses which would very greatly distort a contrast pattern consisting of concentric circles according to FIG. 3e. On the other hand, the radial contrast pattern according to FIG. 3f is much less distorted. Similarly, a drinks bottle with a smooth outside would greatly distort a pattern consisting of vertical lines, at least in its edge region. On the other hand, a pattern consisting of parallel horizontal lines is much less distorted. In the individual case, a suitable contrast pattern must if necessary be determined by means of tests.

What is claimed is:

1. A method for detecting diffusely scattering materials, impurities, deposits, damage or coatings on the surface or fluctuations in the material thickness of containers made from transparent material, the containers being inspected using a light source and an image recording device comprising the steps of:

arranging a contrast pattern between the light source and the containers to be inspected;

producing a reproduction of the containers by means of the image recording device;

scanning the reproduction pointwise to determine image spots;

determining the contrast of the contrast pattern by comparing the brightness of each image spot with that of adjacent image spots; and comparing the number of brightness contrasts in which the determined brightness difference lies below a preset threshold value.

2. The method according to claim 1, wherein the image recording device is focussed on the plane of the contrast pattern.

3. The method according to claim 1 wherein the contrast pattern shows transparent regions and opaque regions which are sharply delimited as compared with each other.

4. The method according to claim 3, wherein the opaque regions block only light of a particular wavelength, and the light of this wavelength is used for the inspection of the containers.

5. A method for detecting diffusely scattering materials, impurities, deposits, damage or coatings on the surface or fluctuations in the material thickness of containers made from transparent material, the containers being inspected using a light source and a camera comprising the steps of:

arranging a contrast pattern between the light source and the containers to be inspected;

producing by means of the camera a reproduction of the containers illuminated through the contrast pattern;

scanning the reproduction pointwise to determine image points;

determining the brightness of each image point;

ascertaining bright-dark and dark-bright transitions between each image point and adjacent image points;

recording the number of transitions and their brightness contrast and comparing the number of transitions having a large brightness contrast with a predetermined threshold value.

6. The method according to claim 5, wherein the camera is focussed on the plane of the contrast pattern.

7. The method according to claim 5 wherein the contrast pattern shows transparent regions and opaque regions which are sharply delimited as compared with each other.

8. The method according to claim 7 wherein the opaque regions block only light of a particular wavelength, and the light of this wavelength is used for the inspection of the containers.

* * * * *